United States Patent [19]

Reinhard et al.

[11] 4,344,865

[45] Aug. 17, 1982

[54] STEAM REGENERATION OF RHODIUM CONTAINING HYDROCARBON DEHYDROCYCLIZATION CATALYSTS

[75] Inventors: Russell R. Reinhard, Hopewell Junction; Tansukhlal G. Dorawala; Edwin R. Kerr, both of Wappingers Falls, all of N.Y.

[73] Assignee: Texaco Inc., White Plains, N.Y.

[21] Appl. No.: 231,820

[22] Filed: Feb. 5, 1981

Related U.S. Application Data

[62] Division of Ser. No. 103,302, Dec. 13, 1979, Pat. No. 4,304,658.

[51] Int. Cl.$^3$ .................... B01J 23/96; C10G 35/06; C10G 35/085
[52] U.S. Cl. .................................. 252/420; 208/136; 585/419
[58] Field of Search .................. 252/420, 411 R; 585/419; 208/136; 423/652

[56] References Cited

U.S. PATENT DOCUMENTS 3,981,794  9/1976  Eberly .................................. 585/419
4,046,869  9/1977  Dorawala et al. .................. 252/420

*Primary Examiner*—P. E. Konopka
*Attorney, Agent, or Firm*—Carl G. Ries; Robert A. Kulason; Carl G. Seutter

[57] ABSTRACT

Steam dehydrocyclization of paraffinic hydrocarbons to aromatic hydrocarbons is effected in the presence of supported catalyst, typically bearing rhodium and preferably chromium and potassium, and characterized by a pH less than about 8.

10 Claims, No Drawings

STEAM REGENERATION OF RHODIUM CONTAINING HYDROCARBON DEHYDROCYCLIZATION CATALYSTS

This is a division of application Ser. No. 103,302, filed Dec. 13, 1979, now U.S. Pat. No. 4,304,658.

FIELD OF THE INVENTION

This invention relates to an improved method of steam dehydrocyclization of a dehydrocyclizable hydrocarbon to prepare aromatic hydrocarbons—and to a catalyst therefor.

BACKGROUND OF THE INVENTION

It has been found to be possible to effect steam dehydrocyclization of paraffinic hydrocarbons by use of supported catalysts which contain a Group VIII noble metal such as rhodium, commonly together with a Group VI B metal such as chromium. Operation with such catalysts is less than totally satisfactory because, while initially quite active and selective, these catalysts deactivate in the steam environment.

It is an object of this invention to provide a method of steam dehydrocyclizing a steam dehydrocyclizable hydrocarbon. It is another object of this invention to provide an improved catalyst for use in such a process. Other objects will be apparent to those skilled in the art.

STATEMENT OF THE INVENTION

In accordance with certain of its aspects, the process of this invention for steam dehydrocyclizing a steam dehydrocyclizable hydrocarbon may comprise contacting said steam dehydrocyclizable hydrocarbon at steam dehydrocyclization conditions with a catalyst composition, having a pH of less than about 8, containing a porous support bearing a catalytic amount of rhodium.

DESCRIPTION OF THE INVENTION

The charge dehydrocyclizable hydrocarbon which may be treated by the process of this invention may be any aliphatic hydrocarbon which is capable of undergoing aromatization, eg dehydrogenation typically with ring closure, to produce an aromatic hydrocarbon which may contain the same or a lesser number of carbon atoms. The charge hydrocarbons which are vaporizable at steam dehydrocyclization temperatures, commonly are aliphatic (including cyclic) hydrocarbons such as paraffins (including naphthenes), olefins, or diolefins. When the charge is a paraffin, it may typically contain 6-20 carbon atoms. Illustrative of such paraffins may be n-hexane, cyclohexane, methylpentanes, heptanes, methylcyclohexane, octanes, methylheptanes, nonanes, decanes etc. Illustrative of the olefins may be hexenes, heptenes, octenes, nonene, etc. Illustrative of the diolefins may be hexadienes, heptadienes, octadienes, etc.

Steam dehydrocyclizable hydrocarbons include those which can cyclize to a six-member ring without prior isomerization. Compounds which cannot thus cyclize (eg methylcyclopentane or isohexane) are dehydrogenated with little or no cyclization.

Commonly the charge dehydrocyclizable hydrocarbon food stream may be one containing a mixture of the above paraffinic and optionally naphthenic components as available in a refinery stream. Illustrative of such streams may be those identified as: naphtha—typically a highly paraffinic straight run naphtha; a paraffinic raffinate from aromatic extraction; a $C_6$ to $C_{10}$ refinery stream; a naphtha fraction having a 140° F.–400° F. boiling range; etc.

Steam dehydrocyclization of the charge hydrocarbon is effected by passing the vaporized charge hydrocarbon together with steam through a catalyst bed at the following conditions:

TABLE

| Condition | Broad Range | Preferred Range | Typical |
|---|---|---|---|
| Temperature °F. | 700–1150 | 850–1100 | 1000 |
| Pressure psig | 0–300 | 50–100 | 70 |
| Steam/Hydrocarbon Mole ratio | 1:1–50:1 | 3:1–20:1 | 7:1 |
| WHSV | 0.1–10 | 0.5–2.0 | 1 |

The catalyst composition which may be employed in practice of the steam dehydrocyclization process of this invention may comprise a catalyst support and, distributed thereon and therein a catalytic amount of (i) rhodium, (ii) optionally a Group VIII non-noble metal, (iii) optionally a Group VI B metal, and (iv) optionally a Group I A metal.

The Group VIII non-noble metal may include iron Fe, cobalt Co, and nickel Ni. Preferably the group VIII metal may be iron.

The Group VI B metal may be chromium Cr, molybdenum Mo, or tungsten W; and in the preferred embodiment, it is chromium Cr.

The Group IA metal, an alkali metal, may be lithium Li, sodium Na, potassium K, rubidium Rb or cesium Cs. In the preferred embodiment, it is potassium K.

The catalyst support may be active or inactive or inert. Typically the support may be a clay, a silica, a metal oxide, a zeolite, etc. The preferred porous material may include alumina, silica, silica-alumina, silica-magnesia, silica-titania, silica-beryllia, silica-zirconia, silica-alumina-magnesia, etc. The preferred support is an inert support such as alumina, (preferably gamma alumina).

In typical practice of the process of this invention the catalyst composition may contain the following components in the parts by weight (expressed as oxide) indicated in the table.

In this table and in the others which follow, the metals are expressed as parts by weight of oxide. Thus, Group VIII—1 part means that the composition contains Group VIII metal in amount sufficient to make 1 part of the corresponding oxide eg NiO or $Fe_2O_3$. The support is expressed as parts by weight of eg alumina.

It will be clear that the metals will be present in the catalyst, not typically in the form of free metal, but as oxide or as other combined form. During the treatment of the catalyst, prior to use, metal oxides in the catalyst may be reduced in whole or in part to free metal.

TABLE

| Component | Broad | Preferred | Typical |
|---|---|---|---|
| Group VIII | 0–40 | 0.5–20 | 1 |
| Group VI B | 0–40 | 5–38 | 10 |
| Group I A | 0–5 | 1–4 | 2 |
| Support | 15–99.9 | 38–88 | 86 |
| Rhodium | 0.1–2.0 | 0.4–1.4 | 1.1 |

The preferred catalyst may be that containing iron-chromium-potassium-aluminum-rhodium; and the catalyst composition may contain the following (expressed as oxide):

TABLE

| Component | Broad | Preferred | Typical |
|---|---|---|---|
| Fe | 0–40 | 0.5–20 | 1 |
| Cr | 0–40 | 10–38 | 10 |
| K | 0–5 | 1–4 | 2 |
| Al | 15–99.9 | 38–88 | 86 |
| Rh | 0.1–2.0 | 0.4–1.4 | 1.1 |

In terms of molar proportions, the catalyst may be represented by the formula: a $(VIII)_{2/n}O$: b $(VI)_{2/m}O$: c $(IA)_2O$: d (Supp): e $(Rh)_{\frac{2}{3}}O$ wherein (VIII) represents a non-noble metal of Group VIII of the Periodic Table having a valence n, (VI) represents a metal of Group VI B of the Periodic Table having a valence m, (IA) represents a metal of Group I A of the Periodic Table, (Rh) represents rhodium, and Supp represents the support. a may be 0–0.75, preferably 0.002–0.38 say 0.019; b may be 0–0.78, preferably 0.1–0.75, say 0.19; c may be 0–0.17, preferably 0.003–0.13, say 0.02; d is 0.15–2.49, preferably 0.38–2.21, say 0.86 and e is 0.0012–0.024, preferably 0.0048–0.0165, say 0.013.

In one preferred embodiment, the catalyst may be represented by the formula a $Fe_{\frac{2}{3}}O$: b $Cr_{\frac{2}{3}}O$: c $K_2O$: d (Supp): e $Rh_{\frac{2}{3}}O$ wherein a is 0–0.75, preferably 0.009–0.37, say 0.018 b is 0–0.78, preferably 0.10–0.75, say 0.20; c is 0–0.5, preferably 0.01–0.04, say 0.02; d is 0.15–2.49, preferably 0.38–2.21, say 0.86 and e is 0.0012–0.024, preferably 0.0048–0.0165, say 0.013.

When the support is alumina, as in the preferred embodiment, the catalyst composition may be represented by the formula a $Fe_{\frac{2}{3}}O$: b $Cr_{\frac{2}{3}}O$: c $K_2O$: d $Al_2O_3$: e $Rh_{\frac{2}{3}}O$ and d may preferably be 0.15–0.93, more preferably 0.38–0.88, say 0.86, and e may be 0.0012–0.024, preferably 0.0048–0.0165 say 0.013.

In practice of this invention, the catalyst may be prepared by immersing a catalyst support in a solution containing the metal ions. The support, typically a gamma-alumina extrudate of 1.5 mm diameter and 10 mm length, may first be steam sintered at 900°–1400° F., say 1110° F. for 5–25 hours, say 12 hours. During sintering, there may be passed through the bed, air at VHSV of 40–600, say 230 together with steam at water VHSV of 0.05–0.10, say 0.06. The steamed alumina is then calcined for 1–5, say 2 hours at 900°–1200° F., say 1000° F. The initial surface of the alumina, typically 200–400, say 231 meter$^2$/gram may be decreased to 70–95%, say about 90% to a value of 140–380, say 192 meter$^2$/gram.

The support (144.4 parts), preferably as so treated above, is cooled to 32°–90° F., say about 75° F. and slurried into 200–2525 parts, say 223.4 parts, of a solution prepared by dissolving soluble decomposable salts of metals of Group VIII and Group VIB in water. Preferably 2–500 parts, more preferably 10–500 parts, say 22.4 parts of a salt of a Group VIB metal, typically chromium trioxide $CrO_3$ and 1–25 parts, preferably 4–25 parts, say 8.0 parts of a salt of a Group VIII metal, typically $Fe(NO_3)_3.9 H_2O$, are dissolved in 30–1000 parts, say 193 parts of water to yield a total solution in amount of 33–1525, say 223.4 parts.

The slurry is mixed for 15 minutes and allowed to stand for 30 minutes. The resulting mixture is dried at 150°–400° F., say 210° F. for up to three days. Further treatment includes heating for 0.5–24 hours, say 3 hours, at 350°–550° F., say 482° F. in a flowing stream of air. This is followed by further heating in air at 800°–1300° F., say 1202° F., for 0.5–24 hours, say three hours.

The resulting mixture above is cooled to 32°–90° F., say 75° F., and then wetted with 180–2400 parts, say 203.4 parts, of a solution prepared by dissolving soluble decomposable salts of rhodium and a Group IA metal in water. Preferably 1–100 parts, more preferable 2–200 parts, say 7.2 parts of a salt of a Group IA metal, typically potassium nitrate $KNO_3$, and 0.5–7 parts, preferably 1–7 parts, say 3.2 parts of a salt of rhodium, typically rhodium chloride $RhCl_3.3H_2O$, are dissolved in 193 parts of water. The wetted mixture in a 1-liter beaker is rotated for ten minutes and then allowed to stand for ten minutes. This rotation/standing procedure is repeated two more times before transferring the wet mixture to an evaporating dish. Visible water is evaporated at about 210° F. followed by oven drying at 300° F. for about 16 hours. The dried catalyst therefrom is then calcined at 900°–1200° F., say 1022° F. for 1–10 hours, say about two hours to yield 149.9–732, say 171 parts of catalyst having a an apparent density of 0.5–1.5, say 0.62. The rhodium may be added to the catalyst system in manner comparable to that by which the other metals are added. It may be added before, with, or after the other metals. Typically it will be added as rhodium nitrate or rhodium chloride $RhCl_3$ although other soluble decomposable salts may be employed. In one embodiment, iron and chromium may be added to the support and after calcining, potassium and rhodium may then be added.

Preferably the rhodium metal may be added as an aqueous solution of rhodium chloride containing 1%–20%, preferably 5%–15%, say 10% of the metal salt.

The product catalyst so prepared may be characterized by the formula a $(VIII)_{2/n}O$: b $(VI)_{2/m}O$: c $(I)_2O$: d (Supp): e $(Rh)_{\frac{2}{3}}O$ wherein all the symbols are as noted supra.

A preferred composition may contain 1% $Fe_{\frac{2}{3}}O$, 10% $Cr_2O_3$, 2% $K_2O$, 1.1% $Rh_{\frac{2}{3}}O$ and 85.9 % $Al_2O_3$. Another preferred composition may contain 1% NiO (or CoO), 10% $Cr_{\frac{2}{3}}O$, 2% $K_2O$, 1.1% $Rh_{\frac{2}{3}}O$, and 85.9% $Al_2O_3$ (or $SiO_2$). Percentages are on a weight basis.

The catalyst composition used in practice of the process of this invention may be prepared by impregnating the support with solutions of rhodium and metals of Groups VIII, VI B, and I A. Typically for example it may be found that the catalyst may be prepared by:

a. impregnating the support sequentially with several solutions each containing one or more of the metals and thereafter drying and calcinating;

b. impregnating the support with one or more solutions containing less than all of the metal (i.e. species or amount), drying and/or calcinating, thereafter impregnating the support with the remaining metals, and drying and/or calcinating etc.

In one embodiment, the catalyst support may thus be prepared by impregnating the support, typically alumina, with one solution containing soluble decomposable salts of the Group VI B and Group IA metals, typically chromium and potassium, drying and calcinating thereafter impregnating the so-obtained pre-catalyst with a colution of a soluble-decomposable salt of the Group VIII metal, typically nickel, and drying and calcining, and thereafter impregnating with a solution of soluble decomposable salt of rhodium, and drying and calcining.

In the preferred embodiment, the catalyst composition may be in the form of pellets, cylinders, or randomly shaped particles, a typical catalyst composition may be in the form of cylinders, of diameter 1-15 mm, say 1.5 mm and height 1-15 mm, say 8-10 mm.

It is a feature of this invention that improved results (particularly in terms of increased conversion and yield at desirably high selectivity) may be achieved by treating the calcined supported catalyst for 4-16 hours, preferably 4-8 hours, say 6 hours in the presence of hydrogen. Treating is effected at high temperature—i.e. at a temperature above that at which the subsequent steam reaction is normally carried out. Although some improvement may be obtained by treating at a temperature of 600°-950° F., it is preferred that treating be carried out at a temperature above that. The preferred temperature at which treating is preferably carried out is 950° F.-1400° F., more preferably 1000° F.-1250° F., say 1060° F. Hydrogen treating by the process of this invention may be carried out at temperatures which are 0°-200° F., say 50° F. higher than those of subsequent reaction.

Treating of the calcined supported catalyst of this invention may preferably be carried out after the catalyst is in place in the reaction vessel. The vessel may be filled with catalyst composition to a bulk density of 50-80 pcf, say 70 pcf. In the treating operation, the catalyst composition is heated to 950°-1400° F., preferably 1000°-1250° F., say 1060° F. in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components including oxygen. It will be apparent that the catalyst, as prepared, contains metals in the oxide state (eg $Rh_3O$); and these may be reduced in whole or in part (eg to Rh metal) during the treating with reducing gas.

This gas may contain (in addition to hydrogen) inert gases such as helium or more preferably light paraffins such as methane, ethane, propane, etc. Hydrogen may be present typically in amount of 30-100 mole %, preferably 80-100 mole %, say 100 mole %, i.e. the preferred embodiment may be that in which the gas consists essentially of hydrogen.

Preferably the catalyst composition may be maintained for 4-16 hours, typically 4-6 hours, say 6 hours in a stream of flowing hydrogen typically flowing at a space velocity VHSV (STP) greater than about 3, more preferably greater than 40, say 40-500, typically 95.

When treating is carried out at atmospheric pressure, as in the preferred embodiment, the partial pressure of hydrogen may be at least about 9 psig (400 mm Hg), preferably 12-15 psia, say 15 psia (760 mm Hg).

Post treating cooling is typically carried out by maintaining the activated catalyst in a stream of flowing steam for 1-10 hours, preferably 1-5 hours, say 2 hours as the temperature is lowered to the reaction temperature of 700°-1150° F. preferably 850°-1100° F. say 1050° F. Preferably steam is present during post-activation in amount of 50-100 mole %, typically 80-100 mole %, say about 100 mole % of the flowing stream.

It is a feature of the novel catalyst of this invention that it may be employed in hydrocarbon conversion processes, typified by steam dehydrocyclization of hydrocarbons with the attainment of unexpected results. Among these may be noted an increase in conversion and yield at a high level of selectivity.

It is a feature of the process of the invention that it be carried out in the presence of a catalyst composition characterized by a pH of less than about 8. In one embodiment, the maximum pH may be 7 and the catalyst may be characterized as acid. The preferred range of pH may be 4.2-7.4, more preferably 4.6-6. Typically steam dehydrocyclization is carried out using a catalyst having a pH of about 5.5.

The pH of the catalyst compositions, as the term is used herein, is determined by charging a 100 ml beaker with 2.0 g of the calcined catalyst and 50 ml of cool distilled water (recently boiled and sealed). The mixture is stirred magnetically at room temperature while inserting a glass pH electrode and a calomel reference electrode. The pH reading is taken when a steady value was indicated by the Beckman Model 42 pH Meter. The meter is calibrated before and after measurement with a standard buffer of 4.0 pH.

If the prepared catalyst composition has a pH of 8 or above, or if it is desired to lower the pH from eg say 7.5 down to about 6, this may be effected by immersing the calcined catalyst (200 parts) in preferably aqueous solution (2000 parts) of low pH for 2-24, preferably 10-20, say 15 hours. The solution may be a solution of an inorganic acid such as nitric acid, hydrochloric acid etc. or of a suitable buffer salt such as eg ammonium chloride or ammonium tartrate.

At the end of the period, the liquid may be poured off and the catalyst composition dried and calcined as before. If the so-treated catalyst is found to possess too high a pH, it may be lowered further by repeating the treatment.

It will be apparent that if the pH of the catalyst composition is found to be less than desired (eg if it be 4 and it is desired to raise it to 6), then the same treatment can be carried out except of course that the solution in which the catalyst composition is immersed may be a basic solution of an inorganic base such as ammonium hydroxide or an organic base such as diethyl amine, pyridine, tetramethyl ammonium hydroxide etc.

It is found that at pH below about 4.6, the initial conversion of n-hexane to aromatics decreases to about 30 mole % (and to less than this as the pH decreases further). As the pH increases from about 4.6 up to about 5.5, the initial conversion increases to about 50 mole %. Above about 5.5 pH, the initial conversion drops again to about 30 mole % at pH of about 6; and as the pH increases further, it thereafter drops further.

In tabular form, based upon comparative runs with catalysts of different pH, the initial conversions may be as follows:

TABLE

| pH | Initial Conversion Mole % of n-hexane |
| --- | --- |
| 4.6 | 30 |
| 4.7 | 37 |
| 5.0 | 40 |
| 5.5 | 52 |
| 5.7 | 38 |
| 5.8 | 34 |
| 6.0 | 30 |

In the preferred embodiment, steam dehydrocyclization, at the conditions hereinabove set forth, permits attainment of aromatic product. The charge hydrocarbon is dehydrogenated and cyclized to form desired aromatic products, typically obtained in conversions of 8%–50%, in yield of 4%–31%, say 21% and in selectivity of 51%–88%, say 80%.

In the case of a typical n-heptane charge, the product (per 100 moles charge) may be

TABLE

| Component | Broad | Preferred | Typical |
|---|---|---|---|
| Unreacted n-heptane | 5–90 | 30–70 | 54.1 |
| Aromatics | 5–75 | 20–60 | 32.5 |
| Other liquids | 0–5 | 0–1 | 0.5 |

DESCRIPTION OF THE PREFERRED EMBODIMENTS

Practice of the process of this invention will be apparent to those skilled in the art from the following illustrative embodiments wherein, as elsewhere in this description, all parts are parts by weight unless otherwise specifically stated.

EXAMPLE I

A catalyst with the nominal composition 1.1% $Rh_{\frac{2}{3}}O$-10% $Cr_2O_3$-2%$K_2O$-1%$Fe_{\frac{2}{3}}O$-85.9% $Al_2O_3$ was prepared according to U.S. Pat. No. 3,436,433 (Example I at column 4, lines 26–41). The calcinated catalyst thus prepared has a pH of 5.4. This catalyst (30 cc, 1/16-inch extrudates) was charged to a one-inch diameter tubular reactor (316 stainless steel). The catalyst was reduced with hydrogen (600 cc./min.) for 16 hours at 1060° F. Preheated steam and n-hexane were charged downflow in vapor phase to the reactor with a nominal mole ratio of 13:1 and a liquid hourly space velocity (hydrocarbon) of Ca 1.5. Reactor temperature and pressure were 1010° F. and 70 psig, respectively. Condensed liquid products were analyzed by gas chromatography, and gases by mass spectrometry. The results are given in the Table which follows and are based on the product collected during the first hour on stream. Total olefin content of the liquid product was 5.6 area %; aromatic content, benzene and toluene, were 41.7 and 1.0 area %, respectively. n-Hexane conversion and aromatic selectivity were calculated by treating $C_6$ olefins (Ca 3.6%) as unconverted n-hexane because of the obvious recycle value of the olefins.

The off-gas from the process contained 85 mole % hydrogen, 8.8 mole % $CO_2$, and 0.7 mole % CO. Corrected to a $C_6$-and-oxides of carbon-free basis, the hydrogen purity was about 94.7 mole %.

EXAMPLE II*–III*

In these control examples, the same catalyst preparation procedure was used as in Example I, except the rhodium component was replaced by an equal weight of palladium (Example II*) and platinum (Example III*) in the catalyst. Platinum was provided as chloroplatinic acid and palladium as palladium nitrate. Using the same feedstock and conditions, both palladium and platinum proved less active and selective for steam dehydrocyclization than rhodium.

*An asterisk here, as elsewhere, indicates a control example.

EXAMPLES IV–V

In these experimental examples, the same catalyst preparation procedure was used as in Example I except for elimination of chromia and iron oxide in Example IV, and the chromia, potassia, and iron oxide in Example V. Evaluating these catalysts as in Example I gave the results shown in the Table. They indicate that although it is possible to utilize rhodium-on-alumina or rhodium-potassium-on-alumina, the presence of chromium and potassia gives unexpected improvement in activity and selectivity of steam dehydrocyclization catalysts.

TABLE

| Example | n-HEXANE$^a$ Charge | $H_2O/HC^b$ | Conv., %$^c$ | Arom. Sel., % | Catalyst pH |
|---|---|---|---|---|---|
| I | 1.1% $Rh_{\frac{2}{3}}O$—10% $Cr_2O_3$—2% $K_2O$—1% $Fe_2O_5/Al_2O_3$ | 13.2 | 50.0 | 79.3 | 5.4 |
| II* | 0.9% Pd—10% $Cr_2O_3$—2% $K_2O$—1% $Fe_2O_3/Al_2O_3$ | 13.6 | 12.1 | 51.5 | |
| III* | 0.9% Pt—10% $Cr_2O_3$—2% $K_2O$—1% $Fe_2O_3/Al_2O_3$ | 14.9 | 5.4 | 23.6 | |
| IV | 1.1% $Rh_{\frac{2}{3}}O$—2% $K_2O/Al_2O_3$ | 12.8 | 41.5 | 67.8 | 6.1 |
| V | 1.1% $Rh_{\frac{2}{3}}O/Al_2O_3$ | 13.9 | 28.4 | 49.0 | 4.3 |

$^a$LHSV 1.5; pressure 70 psig; temperature 1010° F.
$^b$Mole ratio, steam/hydrocarbon.
$^c$Mole percent hydrocarbon charge.
*An asterisk here, as elsewhere, indicates a control example.

In the following examples, the catalysts were evaluated using n-heptane as feedstock at either 925° F. or 1025° F. (each at atmospheric pressure and with a 10:1 mole ratio of steam to hydrocarbon in the feed). The results are shown in the table which follows the examples. They show that comparable results are attained with n-heptane as are attained with n-hexane.

EXAMPLES VI–VIII

The catalyst was prepared as in Example I. Example VI was run at 925° F. (Example VII was run at 1025° F.), atmospheric pressure operation, and a 10:1 mole ratio of steam to hydrocarbon in the feed. The results are given in Table II and indicate that n-hexane and n-heptane give roughly equivalent yields of their corresponding aromatics with this catalyst.

EXAMPLES VIII–X

A catalyst was prepared and evaluated as in Example VI except that chromia was omitted from the catalyst composition. The results are shown in the Table and indicate slightly reduced activity and selectivity as compared to the chromia-containing catalyst; however, this novel composition (without chromia) was entirely regenerable (Example IX) by steaming for 16 hours at 925° F. as shown in the table. Examples VIII and X are for fresh catalyst.

Generally regeneration may be effected by steaming at 800° F.–1200° F., say 925° F. for 12–48 hours, say 16 hours.

EXAMPLES XI–XII

A catalyst with the nominal composition 0.5%Rh₂O-0–40% Cr₂O₃-2%K₂O-57.6% Al₂O₃ was prepared according to U.S. Pat. No. 3,436,434 and evaluated as in Example VI with n-heptane. The results given in the Table indicate that it is less effective as a steam dehydrocyclization catalyst than the 1.1%Rh₂O-10%Cr₂O₃-2%K₂O-1%Fe₂O₃-85.9% Al₂O₃ composition of Example VI.

depending on the feedstock, and in all cases accompanied by a hydrogen-rich by-product gas.

TABLE
STEAM DEHYDROCYCLIZATION

Catalyst-1.1% Rh₂O—10% Cr₂O₃—2% K₂O—1% Fe₂O₃/Al₂O₃
Pressure-70 psig
MHSV-1.5–1.9
Steam/Hydrocarbon Mole Ratio-10–12:1

| Hydrocarbon | Example XV Cyclohexane | Example VI* MCP$^a$ | Example VIII* Isohexane |
|---|---|---|---|

TABLE
n-HEPTANE$^e$

| Example | Catalyst Composition$^b$ | H₂O/HC$^c$ | Temp. °F. | Conv. Mole % | Arom. Sel. Mole % | Catalyst pH |
|---|---|---|---|---|---|---|
| VI | 1.1 Rh₂O—10% Cr₂O₃—2% K₂O—1% Fe₂O₃/Al₂O₃ | 12.1 | 925 | 18.4 | 92.7 | 5.4 |
| VII | 1.1% Rh₂O—10% Cr₂O₃—2% K₂O—1% Fe₂O₃/Al₂O₃ | 10.7 | 1025 | 40.6 | 75.1 | 5.4 |
| VIII | 1.1% Rh₂O—2% K₂O—1% Fe₂O₃/Al₂O₃ | 9.7 | 925 | 14.9 | 82.4 | 7.4 |
| IX | 1.1% Rh₂O—2% K₂O—1% Fe₂O₃ | 9.3 | 925 | 14.8 | 84.2 | 7.4 |
| X | 1.1% Rh₂O—2% K₂O—1% Fe₂O₃/Al₂O₃ | 10.2 | 1025 | 35.7 | 80.3 | 7.4 |
| XI | 0.5% Rh₂O—40% Cr₂O₃—2% K₂O/Al₂O₃ | 14.9 | 925 | 12.8 | 61.2 | 5.7 |
| XII | 0.5% Rh₂O—40% Cr₂O₃—2% K₂O/Al₂O₃ | 9.7 | 1025 | 13.7 | 83.3 | 5.7 |
| XIII* | 0.6% Pt—2% K₂O/Al₂O₃ | 10.0 | 925 | 1.8 | 23.2 | |
| XIV* | 0.6% Pt—2% K₂O/Al₂O₃ | 9.4 | 1025 | 5.5 | 24.9 | |

$^a$LHSV 1.5; pressure 0 psig.
$^b$Nominal weight percentages. Al₂O₃ adds to 100%
$^c$Mole ratio, steam/hydrocarbon.
$^d$Catalyst regenerated by steaming at 925° F. for 16 hours before reuse.
$^e$Includes toluene and benzene; for example in Example VI at 925° F. liquid product contained 4.3 area % benzene and 26.3 area % toluene.

EXAMPLES XIII*–XIV*

Engelhard's RD-150C reforming catalyst, 0.6% Pt on eta-Al₂O₃, was impregnated with KNO₃ and calcined to give a nominal composition of 0.5% Pt-2%K₂O-97.% Al₂O₃. Previous work had shown RD-150C without added alkali to be very quickly and permanently deactivated by steam. As shown in the Table, the addition of 2% K₂O to this catalyst did not suffice to convert it to a good steam dehydrocyclization catalyst.

EXAMPLES XV–XVI*–XVII*

A batch of catalyst with the nominal composition 1.1%Rh₂O-10%Cr₂O₃-2%K₂O-1%Fe₂O₃-85.9%Al₂O₃ was prepared (pH of 4.8) and evaluated as in Example 1 except that the hydrocarbon feedstocks were varied. Instead of n-hexane: cyclohexane (Example XV), methylcyclopentane (Example XVI), and isohexane (Example XVII) were individually and separately charged in separate runs over fresh catalyst. The results, given in the Table which follows, show that cyclohexane is aromatized in high conversion and selectivity even at 925° F. The very low indicated conversions of methylcyclopentane (MCP) and isohexane do not include the formation of C₆ olefins which were 19.5 wt.% for MCP and 9.5 wt.% for isohexane. Aromatic yields for both of these feedstocks did not exceed 1.5 mole % at temperatures as high as 1010° F.

These results show that this steam dehydrocyclization process selectively aromatizes only steam dehydrocyclizable hydrocarbons i.e. only those hydrocarbons which can cyclize to a six-membered ring without prior isomerization, for example, n-hexane, n-heptane, and cyclohexane. Compounds which cannot thus cyclize are simply dehydrogenated to olefins. Thus this process enjoys wide versatility. Depending on the type of feedstock, it may be used to dehydrocyclize paraffins, aromatize naphthenes, or dehydrogenate hydrocarbons which are not aromatic precursors in this sense. In other words, the products may be aromatics or olefins or both

| Temp., °F. | 925 | 1010 | 925 | 1010 | 925 | 1010 |
|---|---|---|---|---|---|---|
| Conv., Mole % | 93.4 | 98.6 | 1.1 | 0.8 | 1.5 | 7.1 |
| Arom. Yld. Mole % | 93.2 | 98.5 | 0.02 | 0.7 | 0.4 | 1.1 |
| Arom. Sel., % | 99.7 | 99.9 | 2.0 | 87.6 | 29.9 | 14.8 |

$^a$Methylcyclopentane.

EXAMPLE XVIII

A paraffinic raffinate obtained by sulfolane extraction of reformate gasoline was subjected to the steam dehydrocyclization process of this invention using the catalyst and conditions described in Example VI and summarized below along with the results.

The charge was sulfolane raffinate which contained 4.63% aromatics by Gas Chromatography. The principal components include C₆–C₁₀ paraffins.

Catalyst was 1.1%Rh₂O-10%Cr₂O₃-2%K₂O-1%Fe₂O₃-Al₂O₃. Temperature was 925° F. at atmospheric pressure. Mole ratio of steam to hydrocarbon 10.1. The hydrocarbon LHSV was 1.5.

| Hourly Cut No. | 1 | 6 |
|---|---|---|
| Wt. % Aromatics in Liquid Product | 12.8 | 7.5 |
| Wt % Aromatics Yield | 8.2 | 2.8 |
| % Aromatic Selectivity | 67.0 | 51.0 |
| Wt. % Coke Yield | 4.0 | 2.7 |

EXAMPLES XIX*–XX

In order to demonstrate the superiority of the catalyst system over illustrative prior art steam dehydrocyclization catalysts, a pair of comparative runs was carried out. In control Example XIX*, a catalyst was prepared according to the procedure of Example I of U.S. Pat. No. 3,461,177 of Box and Hepp. This control catalyst had a nominal composition of 0.5%Pt:2%K₂CO₃/ZnO-Al₂O₃. This catalyst was compared to an experimental (Example XX) catalyst prepared in accordance with Example I supra.

In the comparative runs, charge n-hexane was subjected to steam dehydrocyclization by the process of Example VIII U.S. Pat. No. 3,461,177 i.e. 1010° F. and 70 p.s.i.g. Steam to n-hexane mole ratio was 13. LHSV was 1.5.

The results were plotted to show (i) mole % conversion of n-hexane, (ii) mole % selectivity to aromatics, and (iii) aromatics productivity, expressed as gram-moles per hour per gram of catalyst—each as a function of catalyst age expressed as grams of hexane charged per gram of catalyst.

Except for a brief initial period in the lives of the catalysts, the experimental catalyst of this invention is significantly superior to the control catalyst. For example, at a catalyst age of 5.0 (grams of n-hexane charged per gram of catalyst), the novel catalyst gives a conversion which is twice (26% v. 13%) that of the control catalyst and an aromatics selectivity which is about 38% better (77% v. 56%) than that of the control. Specifically, the experimental catalyst produces $360 \times 10^{-5}$ gram moles of aromatics per hour per gram of catalyst while the prior art control catalyst produces only $75 \times 10^{-5}$ gram moles of aromatics per hour per gram of catalyst.

It should also be noted that the control catalyst deactivates much more quickly than does the experimental catalyst. For example the control, at age 5.0, gives productivity of $7.5 \times 10^{-4}$ while after twice as long (at about age 10), the experimental catalyst gives productivity of about $25 \times 10^{-4}$—almost four times as great.

The prior art catalyst was also found to be less satisfactory in that it produced large amounts of undesired olefins—bromine number of 42.1—while the product attained by the process of the instant invention had a bromine number of only 18.7.

Although this invention has been illustrated by reference to specific embodiments, it will be apparent to those skilled in the art that various changes and modifications may be made which clearly fall within the scope of this invention.

We claim:

1. The method of regenerating a spent catalyst, having a pH of less than about 8 containing a porous support bearing a catalytic amount of rhodium, which has been used to steam dehydrocyclize a steam dehydrocyclizable hydrocarbon at steam dehydrocyclization conditions which comprises steaming said spent catalyst at 800° F.–1200° F. for 12–48 hours thereby forming regenerated catalyst; and recovering said regenerated catalyst.

2. The method of claim 1 wherein said catalyst has a pH of 4.2–7.4.

3. The method of claim 1 wherein said catalyst has a pH of about 4.6–6.0.

4. The method of claim 1 wherein said catalyst has a pH of about 5.5.

5. The method of claim 1 wherein said catalyst contains chromium.

6. The method of claim 1 wherein said catalyst contains a metal of Group I A of the Periodic Table.

7. The method of claim 1 wherein said catalyst contains potassium.

8. The method of claim 1 wherein said catalyst contains a non-noble Group VIII metal.

9. The method of claim 1 wherein said catalyst contains rhodium, potassium, and iron.

10. The method of claim 1 wherein said catalyst contains 0.1 w %–2.0 w % rhodium on a porous alumina support.

* * * * *